(12) United States Patent
Jung et al.

(10) Patent No.: US 7,011,700 B2
(45) Date of Patent: Mar. 14, 2006

(54) ANTIBACTERIAL COLORANT AND INK COMPOSITION COMPRISING THE SAME

(75) Inventors: Yeon-kyoung Jung, Seoul (KR); Seung min Ryu, Gyeonggi-do (KR); Kyung-hoon Lee, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 192 days.

(21) Appl. No.: 10/647,124

(22) Filed: Aug. 25, 2003

(65) Prior Publication Data

US 2004/0103819 A1 Jun. 3, 2004

(30) Foreign Application Priority Data

Aug. 28, 2002 (KR) ...................... 10-2002-0051159

(51) Int. Cl.
*C09D 11/00* (2006.01)
*A01N 55/00* (2006.01)
*A01N 43/50* (2006.01)

(52) U.S. Cl. ................ 106/31.27; 106/31.43; 106/31.49; 106/31.58; 106/31.6; 106/31.75; 106/31.78; 106/31.86; 106/31.87; 514/397; 514/63

(58) Field of Classification Search ............. 106/31.27, 106/31.58, 31.43, 31.49, 31.6, 31.86, 31.75, 106/31.78, 31.87, 15.05, 18.31, 18.32, 18.33; 514/63, 397

See application file for complete search history.

(56) References Cited

U.S. PATENT DOCUMENTS

| | | | | |
|---|---|---|---|---|
| 5,858,079 A | * | 1/1999 | Ohtsu et al. ................. | 106/462 |
| 6,046,330 A | * | 4/2000 | Qinghong et al. ........... | 544/327 |
| 6,331,305 B1 | * | 12/2001 | Sang .......................... | 424/401 |
| 6,537,537 B1 | * | 3/2003 | Deckner et al. .......... | 424/78.02 |
| 6,582,730 B1 | * | 6/2003 | Goswami et al. ............ | 424/520 |
| 6,689,391 B1 | * | 2/2004 | Goswami et al. ............ | 424/559 |
| 2003/0096988 A1 | * | 5/2003 | Goswami et al. .............. | 536/54 |
| 2004/0024037 A1 | * | 2/2004 | Ryu et al. .................... | 514/394 |
| 2005/0080273 A1 | * | 4/2005 | Goswami et al. .............. | 549/23 |

FOREIGN PATENT DOCUMENTS

| | | | |
|---|---|---|---|
| DD | 98944 | * | 7/1973 |
| GB | 1398532 | * | 6/1975 |
| JP | 2002-129074 | | 5/2002 |
| KR | 1995-18328 | | 7/1995 |

OTHER PUBLICATIONS

Derwent abstract of DD 98944 from East; Jul. 1973.*
Derwent abstract of DD 98944 form West; Jul. 1973.*

* cited by examiner

*Primary Examiner*—Helene Klemanski
(74) *Attorney, Agent, or Firm*—Staas & Halsey LLP

(57) ABSTRACT

The present invention relates to an antibacterial colorant and a composition that includes the antibacterial colorant. The antibacterial colorant has at least one functional group and at least one antibacterial moiety bound thereto by an ester bond or an amide bond.

28 Claims, No Drawings

ANTIBACTERIAL COLORANT AND INK COMPOSITION COMPRISING THE SAME

CROSS-REFERENCE TO RELATED APPLICATIONS

This application claims the benefit of Korean Application No. 2002-51159, filed Aug. 28, 2002, in the Korean Intellectual Property Office, the disclosure of which is incorporated herein by reference.

BACKGROUND OF THE INVENTION

1. Field of the Invention

The present invention relates to an antibacterial colorant and a composition containing the same. More particularly, the invention relates to an antibacterial colorant achieved by combining an antibacterial agent with a dye or a pigment and a composition containing the same.

2. Description of the Related Art

Generally, colorants are substances that develop their colors by selectively absorbing or reflecting visible light. Colorants are widely used in a variety of coloration industries, for example, in foods, drugs, cosmetics, paints, ink-jet inks, toners, fibers, leathers, plastics coloration, rubbers coloration, furniture fabrication, textile printing, paper-making, and ceramics. There are two types of colorants: dyes and pigments. Dyes are colored substances that are dissolved and mono-dispersed in water or oil and are bonded to molecules of substrates, such as fibers, for coloration. Pigments are not dissolved in water or oil, and thus, pigment powders form opaque colored films on the surfaces of substrates. Conventionally, dyes provide a wide color gamut and a bright and clear color. However, decoloration or discoloration by light and running of colors in water or organic solvents are likely to occur. Therefore, dyes have poor light and water resistance. On the other hand, pigments have better light and water resistance than dyes. However, when pigments are exposed to ultraviolet light from the sun or the like for an extended period of time, the pigments may become decolored. In addition, pigments provide a narrower color gamut and types of pigments are not diversified, relative to dyes.

An ink composition containing dye or pigment faces another problem when bacteria are generated in ink, deteriorating the quality of ink and storage stability. For these reasons, antibacterial agents are separately added to compositions containing colorants in an attempt to avoid the generation and growth of bacteria. However, such antibacterial agents lower the stability of the compositions, thus generating precipitates. Therefore, it is difficult to ensure consistencies of the compositions. In addition, when the compositions are projected onto substrates through small-sized orifices, in particular, as in ink-jet printing, the orifices are easily clogged due to coagulation of the compositions.

SUMMARY OF THE INVENTION

An aspect of the present invention is to provide a colorant that contains antibacterial characteristics by combining antibacterial agents with colorant molecules and to provide a composition that includes the same.

To achieve the above stated goal, the present invention provides an antibacterial colorant comprising a colorant molecule having at least one functional group and at least one antibacterial moiety bound thereto by an ester bond or an amide bond.

Preferably, the antibacterial agent originates from carbendazim derivatives as represented by Chemical Formula 1.

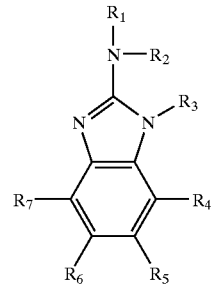

Chemical Formula 1 wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms.

Also, the invention provides a composition comprising the antibacterial colorant having at least one functional group and at least one antibacterial moiety bound thereto by an ester bond or an amide bond.

Additional aspects and advantages of the invention will be set forth in part in the description which follows and, in part, will be obvious from the description, or may be learned by practice of the invention.

DETAILED DESCRIPTION OF THE EMBODIMENTS

The invention is further described in detail below.

The antibacterial colorant of the invention is formed by bonding an antibacterial agent with a colorant, thus adding antibacterial characteristics to the colorant. In particular, antibacterial agents such as carbendazim derivatives or silane derivatives are reacted and bonded with dye or pigment having at least one functional group, such as an amino group, a hydroxy group, a carboxyl group, a phosphoric acid group or a sulfonic acid group so that the resultant molecules possess the antibacterial character. Further, the invention provides prolonged storage stability without adding a separate antibacterial agent during the production of ink. Moreover, since hydroxy or carboxyl groups, which are water soluble functional groups, are replaced with amide or ester groups, the water resistance is enhanced.

The antibacterial colorant of the present invention is formed by combining an antibacterial agent with a colorant.

The preferred antibacterial agent is carbendazim derivatives in the Chemical Formula 1 or silane derivatives. The molecules of these derivatives contain at least one functional group that is able to make an amide or an ester bond with a carboxyl group, a hydroxy group, an amino group or a sulfonic acid group or a phosphoric acid group contained in a molecule of a dye or a pigment and gives an antibacterial characteristic to the colorant.

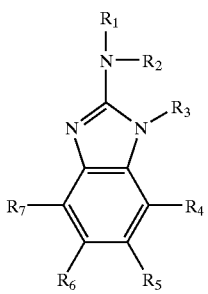

Chemical Formula 1 wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms.

A preferred antibacterial agent, a chemical compound of Chemical Formula 1, may be represented by Chemical Formula 3.

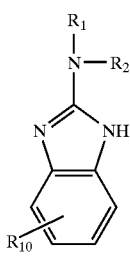

Chemical Formula 3 wherein $R_1$ is selected from the group consisting of a hydrogen atom, a hydroxy group or a carboxyl group, and $R_2$ and $R_{10}$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a sulfonic acid group or salts thereof, a phosphoric acid group or salts thereof, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms.

The preferred antibacterial agent may be a silane compound of Chemical Formula 2.

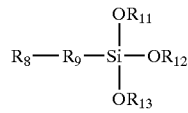

Chemical Formula 2 wherein $R_8$ is selected from the group consisting of a hydrogen atom, a hydroxy group, an amino group, a carboxyl group or salts thereof, and a sulfonic acid group or salts thereof, and $R_9$ represents a heteroatom of —O—, —N—, —S—, or —P—, a substituted or an unsubstituted alkylene group with 1 to 30 carbon atoms, substituted or unsubstituted alkenylene or substituted or unsubstituted alkynylene groups with 2 to 30 carbon atoms, a substituted or an unsubstituted heteroalkylene group with 1 to 30 carbon atoms, a substituted or an unsubstituted arylene group with 6 to 30 carbon atoms, a substituted or an unsubstituted arylalkylene group with 6 to 30 carbon atoms, a substituted or an unsubstituted heteroarylene group with 6 to 30 carbon atoms, a substituted or an unsubstituted heteroarylalkylene group with 6 to 30 carbon atoms, and $R_{11}$, $R_{12}$, and $R_{13}$ each independently is selected from the group consisting of a hydrogen atom, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms.

The antibacterial agent, as described above, reacts and bonds with the functional group of the colorant molecules, such as an amino group, a carboxyl group, a hydroxy group, a phosphoric acid group or a sulfonic acid group to form an antibacterial colorant in accordance with Reaction Schemes 1 to 4 below.

Reaction Scheme 1

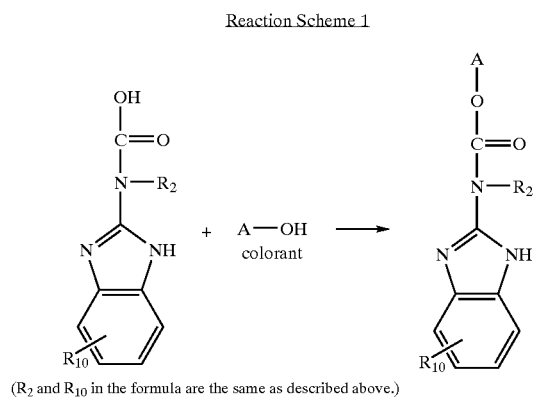

($R_2$ and $R_{10}$ in the formula are the same as described above.)

Reaction Scheme 2

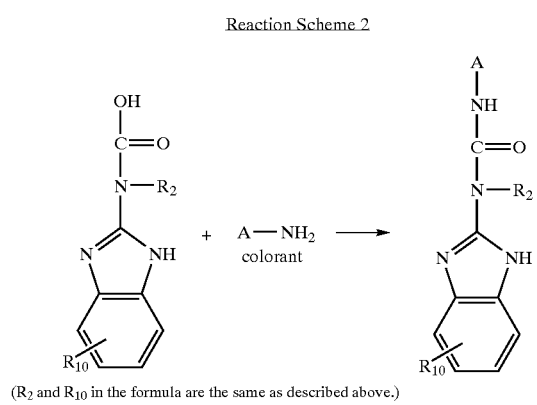

($R_2$ and $R_{10}$ in the formula are the same as described above.)

Reaction Scheme 3

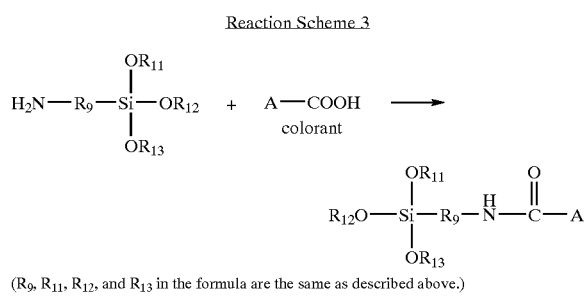

($R_9$, $R_{11}$, $R_{12}$, and $R_{13}$ in the formula are the same as described above.)

Reaction Scheme 4

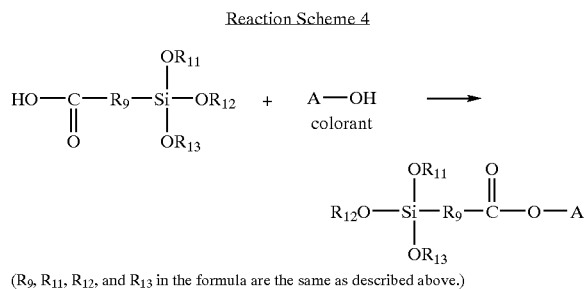

($R_9$, $R_{11}$, $R_{12}$, and $R_{13}$ in the formula are the same as described above.)

A common colorant to be coupled with the antibacterial agent may be any dye or pigment conventionally used in a variety of coloration industries such as in toners, inks, fibers, paints, and plastics coloration provided that an amino, a carboxyl, a hydroxyl, a phosphoric acid group or a sulfonic acid group is present in a molecule of the dye or the pigment. Examples of suitable dyes include C.I. Direct Black 9, 17, 19, 22, 32, 51, 56, 91, 94, 97, 166, 168, 173, 199, C.I. Direct Blue 1, 10, 15, 22, 77, 78, 80, 200, 201, 202, 203, 207, 211, C.I. Direct Red 2, 4, 9, 23, 31, 39, 63, 72, 83, 84, 89, 111, 173, 177, 184, 240, and C.I. Direct Yellow 8, 9, 11, 12, 27, 28, 29, 33, 35, 39, 41, 44, 50, 53, 58, but are not limited to the ones specified. Examples of suitable pigments include carbon black, graphite, vitreous carbon, activated charcoal, activated carbon, anthraquinone, phthalocyanine blue, phthalocyanine green, diazos, monoazos, pyranthrones, perylene, quinacridone, and indigoid pigments, but are not limited to the ones specified.

The alkyl group used as the R group of the present invention includes linear or branched radicals with 1 to 30 carbon atoms. The preferred alkyl radical is a linear or branched radical with 1 to 20 carbon atoms. A more preferred alkyl radical has 1 to 12 carbon atoms. Examples of suitable radicals include methyl, ethyl, n-propyl, isopropyl, n-butyl, isobutyl, sec-butyl, t-butyl, pentyl, iso-amyl, hexyl, heptyl, octyl, nonyl, decyl, and dodecyl. Further, more than one hydrogen atom in the alkyl group may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid group or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The alkenyl or alkynyl groups used as the R group of the present invention are formed when any of the previously listed alkyl group contains double or triple carbon bonds in the middle or at the end of the chain. Examples include ethylene, propylene, butylenes, hexylene and acetylene. More than one hydrogen atom in these alkenyl or alkynyl groups may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The heteroalkyl groups used as the R group of the present invention are formed when any of the previously listed alkyl group contains a nitrogen atom, a sulfur atom, an oxygen atom or a phosphor atom. Examples include methoxy, ethoxy, propoxy, butoxy and t-butoxy. Examples of a substituted heteroalkyl group include haloalkoxy radicals such as fluoromethoxy, cloromethoxy, trifluoromethoxy, trifluoroethoxy, fluoroethoxy and fluoropropoxy. More than one hydrogen atom in these heteroalkyl groups may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The aryl groups as the R group of the present invention are carbocycle aromatic systems with 6 to 30 carbon atoms in one or more ring structures, and may be used solely or in a combination. These rings may be held together by the pendant method or fused together. The term "aryl" includes phenyl, naphtyl, tetrahydronaphtyl, indenyl, biphenyl and other similar aromatic radicals. A more preferred aryl is a phenyl or a naphtyl. The aryl group may have substituents such as a hydroxy, a halo, a haloalkyl, a nitro, a cyano, an alkoxy or a lower alkylamiNo. More than one hydrogen atom in the aryl groups may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid group or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The arylalkyl groups as the R group of the present invention are formed when one or more of the hydrogen atoms of the previously listed aryl group are substituted with lower alkyl radicals, such as methyl, ethyl or propyl radicals. Examples include benzil and phenylethyl. More than one hydrogen atom in the arylalkyl groups may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid group or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The heteroaryl groups as the R group of the present invention include 1, 2 or 3 heteroatoms chosen from N, O, P and S and further include cyclic atoms with 6 to 30 carbon cyclic atoms, wherein at least one is a monocyclic or a bicyclic aromatic radical. Examples include thienyl, benzotienyl, pyridyl, pyrazinyl, pyramidinyl, pyridazinyl, quinolinyl, quinoxalinyl, imidazolyl, furanyl, benzofuranyl, thiazole, isoxazolyl, benzisoxazolyl, benzimidazolyl, triazolyl, pirazolyl, pyrolyl, indolyl, 2-pyridonyl, 4-pyridonyl, N-alkyl-2-pyridonyl, pyrazinonyl, pyridazinonyl, pyrimidinonyl, oxazolonyl, corresponding N-oxides (for example, pyridyl N-oxide and quinolinyl N-oxide) and tertiary salts thereof, but are not limited to the ones specified. More than one hydrogen atom among these heteroatoms may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid group or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The heteroarylalkyl groups as the R group of the present invention are formed by substituting one or more of the hydrogen atoms of the previously listed heteroaryl group with an alkyl group. More than one hydrogen atom of the heteroarylalkyl group may be replaced with a halogen atom, a hydroxy group, a nitro group, a cyano group, an amino group, an amidino group, a hydrazine, a hydrazone, a carboxyl group or salts thereof, a sulfonic acid group or salts thereof, a phosphoric acid group or salts thereof, an alkyl group with 1 to 20 carbon atoms, an alkenyl group with 2 to 20 carbon atoms, an alkynyl group with 2 to 20 carbon atoms, a hetroalkyl group with 1 to 20 carbon atoms, an aryl group with 6 to 20 carbon atoms, an arylalkyl group with 6 to 20 carbon atoms, a heteroaryl group with 6 to 20 carbon atoms, and a heteroarylalkyl group with 6 to 20 carbon atoms.

The definition of the substituents used in the present invention, such as an alkylene, an alkenylene, a heteroalkylene, an arylene, an arylalkylene, a heteroarylene and a heteroarylalkylene are the same as the previously discussed definitions of an alkyl, an alkenyl, a heteroalkyl, an aryl, an arylalkyl, a heteroaryl and a heteroarylalkyl respectively, except for the fact that the radicals are not joined at the end of the chain, but in the middle of the chemical chain.

The present invention also provides a composition containing the above-described antibacterial colorant obtained by coupling a common colorant with an antibacterial agent. The antibacterial colorant-containing composition of the present invention has excellent antibacterial quality even in the absence of an antibacterial agent for enhancement of antibacterial quality. Therefore, side effects caused by the addition of an antibacterial agent to a conventional colorant-containing composition are prevented. That is, lowering of composition stability and precipitate generation are prevented. In particular, when the antibacterial colorant-containing composition of the present invention is projected onto a substrate through a small-sized orifice, clogging of the orifice by composition coagulation infrequently occurs. Therefore, a substrate to which the antibacterial colorant-containing composition of the present invention is applied may preserve excellent antibacterial quality for a long term.

The antibacterial colorant of the present invention may be used in a variety of coloration industries, for example, in toners, paints, ink-jet inks, coatings, fibers, leathers, plastics coloration, rubbers coloration, textile printing, paper-making, and ceramics. Hereinafter, an ink composition, as an illustrative embodiment of the antibacterial colorant-containing composition, will be described in detail, but the present invention is not limited thereto.

The ink composition of the present invention may comprise the antibacterial colorant of Formula 1, a carrier medium, and/or an additive.

A preferred amount of the antibacterial colorant may be 1 to 20 parts by weight per 100 parts by weight of the ink composition.

The carrier medium may be water, one or more organic solvents, or a mixture thereof. When the carrier medium is a mixture of water with one or more organic solvents, the content of the organic solvent may be 5 to 50 parts by weight based on 100 parts by weight of the ink composition.

The contents of the water and the organic solvent depend on various factors, for example viscosity, surface tension, and drying speed of the ink composition. The contents may also vary depending on a printing method and type of a substrate on which the ink is printed.

Examples of the organic solvent for the aqueous medium include:

alcohols such as methylalcohol, ethylalcohol, n-propylalcohol, isopropylalcohol, n-butylalcohol, sec-butylalcohol, and t-butylalcohol, isobutylalcohol;

ketones such as acetone, methylethylketone, diacetonealcohol;

esters such as ethyl acetate and ethyl lactate;

a polyhydric alcohol such as ethyleneglycol, diethyleneglycol, triethyleneglycol, propyleneglycol, butyleneglycol, 1,4-butandiol, 1,2,4-butantriol, 1,5-pentandiol, 1,2,6-hexantriol, hexyleneglycol, glycerol, glycerol ethoxylate, and trimethylolpropane ethoxylate;

a lower alkylether such as ethyleneglycol monomethylether, ethyleneglycol monoethylether, diethyleneglycol methylether, diethyleneglycol ethylether, triethyleneglycol monomethylether, and triethyleneglycol monoethyl ether;

a nitrogen containing compound such as 2-pyrrolidone and N-methyl-2-pyrrolidone; and a sulfur containing compound such as dimethyl sulfoxide, tetramethylene sulfone and thioglycol.

The ink composition of the present invention may further include an additive such as a dispersing agent, a viscosity control agent, a surfactant, a storage stabilizer, a humectant, and a metallic oxide.

At least one dispersing agent is added to the ink composition to secure dispersion stability of the colorant. However, there are no particular limitations on the dispersing agent. In addition to using a dispersing agent with a low molecular weight and a simple structure, even dispersing agents with a high molecular weight such as a block copolymer may be utilized.

Examples of the dispersing agent with a comparatively low molecular weight and simple chemical structure include polyvinylalcohol (PVA), cellulosics, ethylene oxide modified phenols, an ethylene oxide polymer, a propylene oxide polymer, a sodium polyacrylate solute, a modified polyacrylate resin solute, a solute of an alkylolammonium salt of a low molecular weight polycarboxylic acid polymer, a solute of an alkylolammonium salt of a polyfunctional polymer or any combination of the foregoing, but suitable dispersing agents are not limited to the ones specified.

Further, examples of a dispersing agent with a complex structure and a high molecular weight include a siloxane based polymer such as a polyether siloxane copolymer. The structure may be in AB or BAB form. A may be a hydrophobic homopolymer of a substituted or an unsubstituted acrylic monomer with 1 to 30 carbon atoms or a copolymer. B may be a hydrophilic polymer of a substituted or an unsubstituted acrylic monomer with 1 to 30 carbon atoms or a copolymer. In detail, an acrylic acid/acrylate copolymer, a metacrylic acid/metacrylate copolymer, an acrylic acid/polydialkylsiloxane/acrylate block copolymer or any combination of the foregoing may be used, but suitable dispersing agents with a complex structure and a high molecular weight are not limited to the ones specified.

Preferably, the dispersing agent may be included in the ink composition in an amount of 0.1 to 10 parts by weight per 100 parts by weight of the ink composition.

The viscosity control agent is a material that controls the viscosity for smooth jetting of the ink composition. Examples of viscosity control agents include casein and carboxymethylcellulose. The content of the viscosity agent in the ink composition may be 0.1 to 5 parts by weight per 100 parts by weight of the dispersing agent.

A surfactant controls the surface tension to stabilize the jetting capacity at the nozzle. Anionic, nonionic or cationic surfactants may be used.

Examples of an anionic surfactant include:

alkylcarboxylic acid salts with 1 to 1000 carbon atoms, preferably 10 to 200 carbon atoms;

alcohol sulfonic acid ester salts with 1 to 1000 carbon atoms, preferably 10 to 200 carbon atoms;

alkyl sulfonic acid salts with 1 to 1000 carbon atoms, preferably 10 to 200 carbon atoms; and alkylbenzene sulfonic acid salts with 1 to 1000 carbon atoms, preferably 10 to 200 carbon atoms.

Examples of a nonionic surfactant include:

polyoxyethylene alkyl ether where the alkyl has 1 to 1000 carbon atoms, preferably 10 to 200 carbon atoms;

polyoxyethlene alkyl phenyl ether where the alkyl has 1 to 1000 carbon atoms, preferably 10 to 200 carbon atoms;

polyoxyethlene secondary alcohol ether;

polyoxyethlene oxypropylene block copolymer;

polyglycerine fatty acid ester; and sorbitan fatty acid ester.

Examples of a cathonic surfactant include:

aliphatic amine salts, quaternary ammonium salt, alkylpyridinium salts, and so forth.

Various combinations of these surfactants may be used. The preferred amount of the surfactant is 0.1 to 5 parts by weight per 100 parts by weight of the ink composition.

The humectant acts to prevent clogging of the ink composition at the nozzle. Polyhydric alcohols are used to perform such a function. Examples include glycerin, ethylene glycol, diethylene glycol, triethiene glycol, propylene glycol, dipropylene glycol, hexylene glycol, 1,3-butandiol, 1,4-butandiol, 1,5-pentandiol, 2-butene-1,4-diol, 2-methyl-2-pentandiol and any combination thereof. The preferred amount of the humectant is 2 to 30 parts by weight per 100 parts by weight of the ink composition.

The composition of the present invention may be prepared using the components as mentioned above and using the following procedure.

First, the above-described antibacterial colorant is added to a carrier medium, and, if necessary, additives such as a dispersing agent, a viscosity modifier, and a surfactant are added thereto and mixed. The obtained mixture is thoroughly stirred in an agitator until a homogeneous mixture is obtained. Then, the homogeneous mixture is filtered through a filter with a pore size of 0.45 to 1.0 $\mu$m to prepare the ink composition of the present invention.

The invention will be further described in detail through the following examples. However, the present invention is not limited to these examples.

EXAMPLE 1

26.5 g of C.I. Direct Black 168, 300 ml of DMSO, and 21.3 g of carbendazim derivative of Chemical Formula 11 were placed in a 500 ml Erlenmeyer flask and dissolved. 1–2 boiling chips were added, then, 30 ml of concentrated sulfuric acid were slowly added the mixture. The flask containing the mixture was connected to a reflux apparatus and the mixture was reacted for over 8 hours at 80° C. The resulting mixture was cooled to room temperature. An excess amount of methanol was added and the resulting crystals were filtered through a suction filter. To remove any non-reactant, the crystals were re-dissolved in DMSO, and methanol was added. The resulting crystals were then filtered through a suction filter and were dried in an oven to obtain 27.4 g of the antibacterial colorant of Chemical Formula 12.

Chemical Formula 11

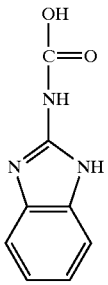

Chemical Formula 12

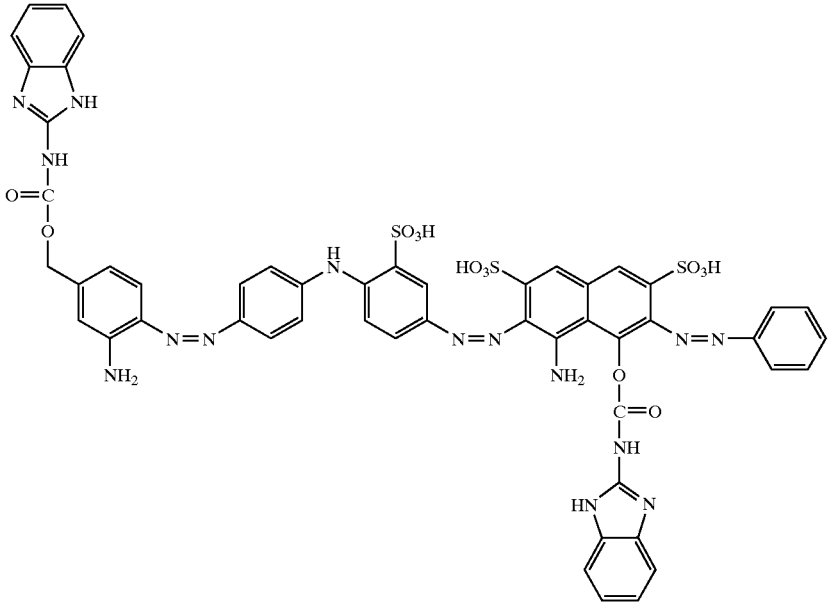

EXAMPLE 2

100 ml of DMSO and 13.4 g of carbendazim derivative of Chemical Formula 11 were placed in a 500 ml Erlenmeyer flask and dissolved. 7.1 g of $SOCl_2$ were then added, and the compounds were reacted at room temperature for over 1 hour to obtain solution (A). 23.0 g of C.I. Pigment Red 177 was melted in 200 ml of DMSO, then added to solution (A) along with 1–2 boiling chips. The flask containing the mixture was connected to a reflux apparatus, and the mixture was reacted for over 6 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 21.6 g of the antibacterial colorant of Chemical Formula 13.

Chemical Formula 13

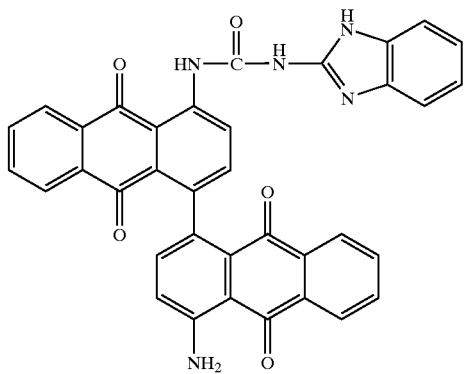

EXAMPLE 3

100 ml of DMSO, and 16.7 g of 3-amino-propyltriethoxysilane of Chemical Formula 14 were placed in a 500 ml Erlenmeyer flask and dissolved. 7.1 g of $SOCl_2$ were then added and reacted at room temperature for over 1 hour to obtain solution (B). 28.7 g of C.I. Direct Black 51 was melted in 200 ml of DMSO, then added to solution (B) along with 1–2 boiling chips. The flask was connected to a reflux apparatus, and the mixture was reacted for over 6 hours at 80° C. The resulting mixture was cooled to room temperature. An excess amount of methanol was added and the resulting crystals were filtered through a suction filter. To remove any non-reactant, the crystals were re-dissolved in DMSO and methanol was added. The resulting crystals were then filtered through a suction filter and were dried in an oven to obtain 27.2 g of the antibacterial colorant of Chemical Formula 15.

EXAMPLE 4

300 ml of DMSO, 33.1 g of C.I. Direct Black 168, and 16.7 g of 3-amino-propyltriethoxysilane were placed in a 500 ml Erlenmeyer flask and dissolved. 1–2 boiling chips were added to the solution and 30 ml of concentrated sulfuric acid were added dropwise. The flask was connected to a reflux apparatus, and the mixture was reacted for over 8 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 30.3 g of the antibacterial colorant of Chemical Formula 16.

Chemical Formula 14

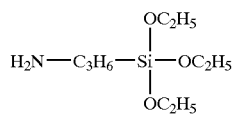

Chemical Formula 15

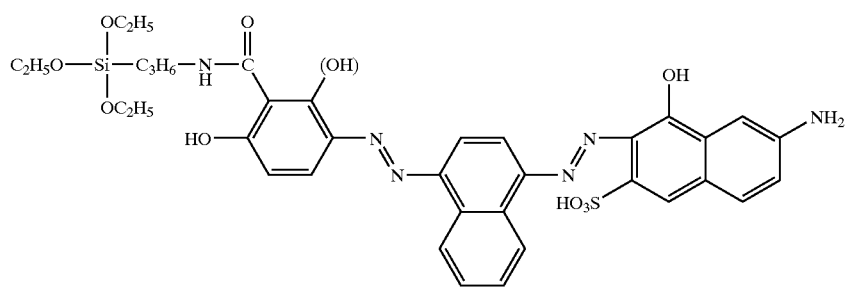

Chemical Formula 16

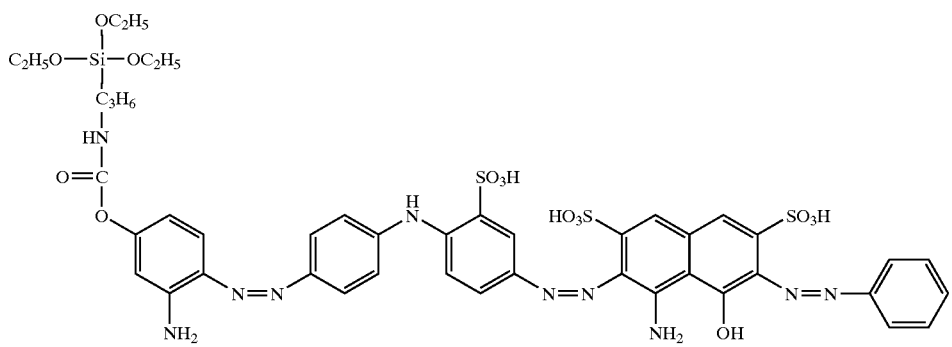

EXAMPLE 5

100 ml of DMSO, and 8.53 g of carbendazim derivative of Chemical Formula 17 were placed in a 500 ml Erlenmeyer flask and dissolved. 4.2 g of SOCl$_2$ were then added and reacted at room temperature for over 1 hour to obtain solution (C). 23.8 g of C.I. Acid Black 191 was melted in 200 ml of DMSO, then, added to solution (C) along with 1–2 boiling chips. The flask was connected to a reflux apparatus, and the mixture was reacted for over 6 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 19.5 g of the antibacterial colorant of Chemical Formula 18.

EXAMPLE 6

100 ml of DMSO, and 24.2 g of silane chemical compound of Chemical Formula 19 were placed in a 500 ml Erlenmeyer flask and dissolved. 12.3 g of SOCl$_2$ were then added and reacted at room temperature for over 1 hour to obtain solution (D). 21.4 g of C.I. Acid Yellow 23 was melted in 200 ml of DMSO, and then was added to solution (D) along with 1–2 boiling chips. The flask was connected to a reflux apparatus, and the mixture was reacted for over 6 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 25.7 g of the antibacterial colorant of Chemical Formula 20.

$$H_2N-C_2H_5OC_2H_5-Si(OC_2H_5)_3 \quad \text{Chemical Formula 19}$$

Chemical Formula 17

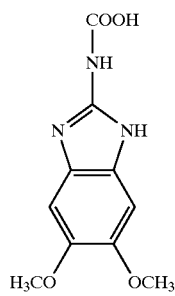

Chemical Formula 18

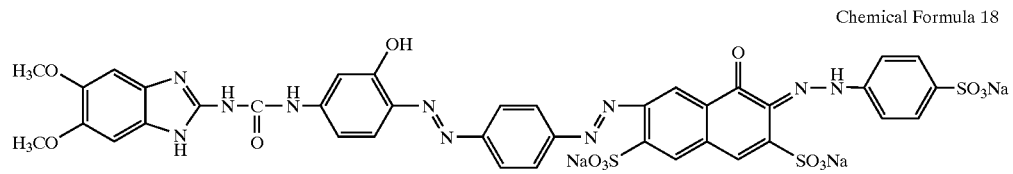

Chemical Formula 20

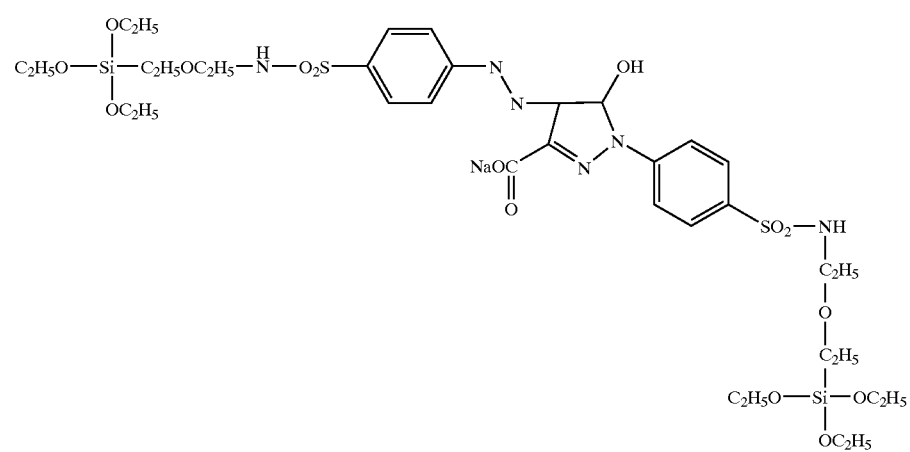

EXAMPLE 7

100 ml of DMSO, and 10.6 g of carbendazim derivative of Chemical Formula 21 were placed in a 500 ml Erlenmeyer flask and dissolved. 7.7 g of SOCl₂ were then added and reacted at room temperature for over 1 hour to obtain solution (E). 21.5 g of C.I. Pigment Red 57 was melted in 200 ml of DMSO, and then was added to solution (E) along with 1–2 boiling chips. The flask was connected to a reflux apparatus, and the mixture was reacted for over 6 hours at 80° C. The resulting mixture was cooled to room temperature. An excess amount of methanol was added and the resulting crystals were filtered through a suction filter. To remove any non-reactant, the crystals were re-dissolved in DMSO, and methanol was added. The resulting crystals were then filtered through a suction filter and were dried in an oven to obtain 20.1 g of the antibacterial colorant of Chemical Formula 22.

Chemical Formula 21

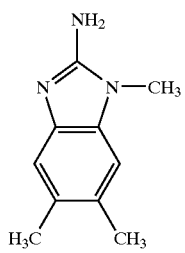

Chemical Formula 22

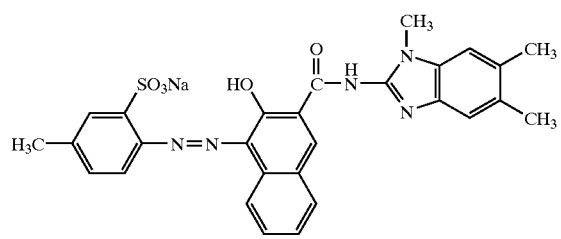

EXAMPLE 8

100 ml of DMSO, and 8.9 g of silane chemical compound of Chemical Formula 23 were placed in a 500 ml Erlenmeyer flask and dissolved. 4.6 g of SOCl₂ were then added and reacted at room temperature for over 1 hour to obtain solution (F). 24.7 g of C.I. Pigment Black 7 was melted in 200 ml of DMSO, and then was added to solution (F) along with 1–2 boiling chips. The flask was connected to a reflux apparatus, and the mixture was reacted for over 6 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 22.0 g of the antibacterial colorant of Chemical Formula 24.

Chemical Formula 23

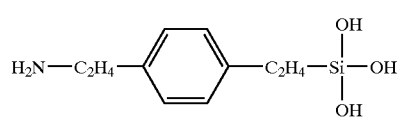

Chemical Formula 24

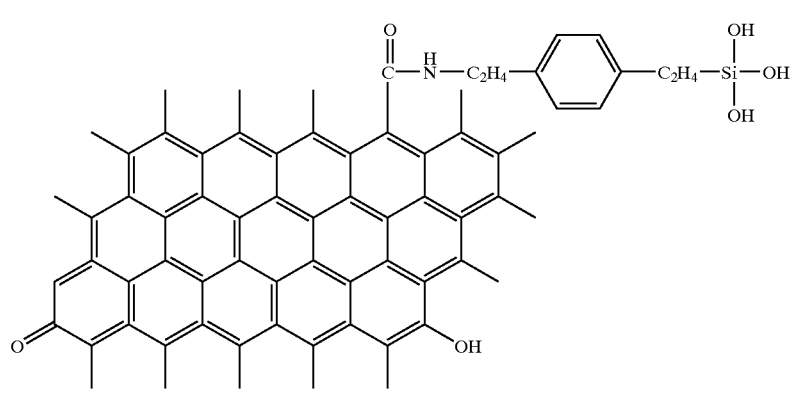

EXAMPLE 9

300 ml of DMSO, 21.4 g of C.I. Acid Yellow 23, and 24.2 g of carbendazim derivative of Chemical Formula 25 were placed in a 500 ml Erlenmeyer flask and dissolved. 1–2 boiling chips were added to the solution, and 30 ml of concentrated sulfuric acid were slowly added dropwise. The flask was connected to a reflux apparatus, and the mixture was reacted for over 8 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 26.0 g of the antibacterial colorant of Chemical Formula 26.

EXAMPLE 10

300 ml of DMSO, 22.9 g of C.I. Direct Black 51, and 16.2 g of silane chemical compound of Chemical Formula 27 were placed in a 500 ml Erlenmeyer flask and dissolved. 1–2 boiling chips were added to the solution, and 30 ml of concentrated sulfuric acid were added dropwise. The flask was connected to a reflux apparatus, and the mixture was reacted for over 8 hours at 80° C. The resulting mixture was cooled to room temperature. An excess amount of methanol was added, and the resulting crystals were filtered through a suction filter. To remove any non-reactant, the crystals were re-dissolved in DMSO, and methanol was added. The resulting crystals were then filtered through a suction filter and were dried in an oven to obtain 22.5 g of the antibacterial colorant of Chemical Formula 28.

Chemical Formula 25

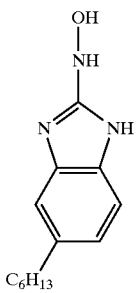

Chemical Formula 26

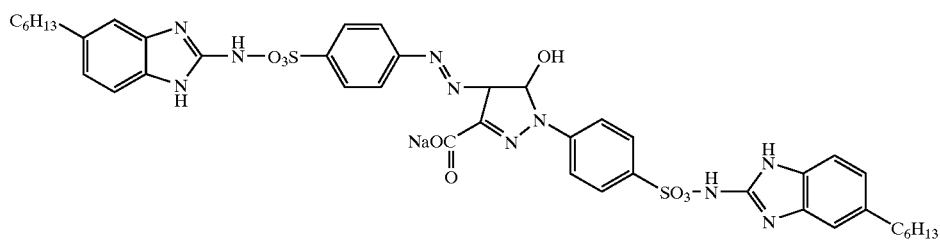

Chemical Formula 27

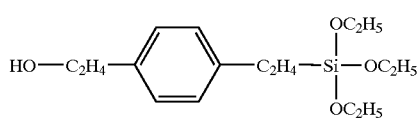

Chemical Formula 28

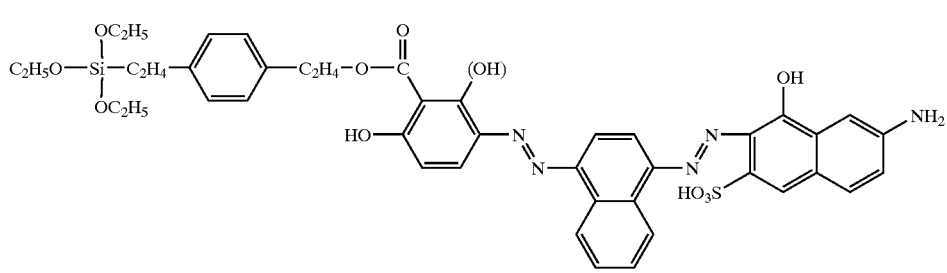

EXAMPLE 11

| Composition: | |
|---|---|
| Antibacterial colorant of Chemical Formula 12 | 4.0 g |
| Water | 77.0 g |
| Isopropyl alcohol | 3.0 g |
| Ethyleneglycol | 10.0 g |
| Glycerine | 6.0 g |

The above ingredients were mixed with stirring over 30 minutes until the solution was uniform. The resulting solution was filtered through a 0.45 μm filter to obtain an ink composition.

EXAMPLE 12

The same method was used as in Example 11, except that instead of using the antibacterial colorant of Chemical Formula 12, the antibacterial colorant of Chemical Formula 13, as produced in Example 2, was used to obtain an ink composition. Additionally, 3.0 g of TEGO dispers 750W was added as a dispersing agent, and thus, the amount of water was reduced to 74.0 g, and a 0.8 μm filter was used.

EXAMPLE 13

The same method was used as in Example 11, except, instead of using the antibacterial colorant of Chemical Formula 12, the antibacterial colorant of Chemical Formula 15, as produced in Example 3, was used to produce the ink composition.

EXAMPLE 14

The same method was used as in Example 11, except, instead of using the antibacterial colorant of Chemical Formula 12, the antibacterial colorant of Chemical Formula 16, as produced in Example 4, was used to produce the ink composition.

EXAMPLE 15

The same method was used as in Example 11, except, instead of using the antibacterial colorant of Chemical Formula 12, the antibacterial colorant of Chemical Formula 18, as produced in Example 5, was used to produce the ink composition.

EXAMPLE 16

The same method was used as in Example 11, except, instead of using the antibacterial colorant of Chemical Formula 12, the antibacterial colorant of Chemical Formula 20, as produced in Example 6, was used to produce the ink composition.

EXAMPLE 17

The same method was used as in Example 11, except, instead of using the antibacterial colorant of Chemical Formula 12, the antibacterial colorant of Chemical Formula 22, as produced in Example 7, was used to produce the ink composition. Additionally, 3.0 g of TEGO dispers 750W was added as the dispersing agent, and thus, the amount of water was reduced to 74.0 g, and a 0.8 μm filter was used.

EXAMPLE 18

The same method was used as in Example 11, except, instead of using the antibacterial colorant of Chemical Formula 12, the antibacterial colorant of Chemical Formula 24, as produced by the method in Example 8, was used to produce the ink composition. Additionally, 3.0 g of TEGO dispers 750W was added as the dispersing agent, and thus, the amount of water was reduced to 74.0 g, and a 0.8 μm filter was used.

EXAMPLE 19

The same method was used as in Example 11, except, instead of using the antibacterial colorant of Chemical Formula 12, the antibacterial colorant of Chemical Formula 26, as produced in Example 9, was used to produce the ink composition.

EXAMPLE 20

The same method was used as in Example 11, except, instead of using the antibacterial colorant of Chemical Formula 12, the antibacterial colorant of Chemical Formula 28, as produced in Example 10, was used to produce the ink composition.

COMPARATIVE EXAMPLE 1

The same method was used as in Example 11, except, instead of using the antibacterial colorant of Chemical Formula 12, C.I. Direct Black 168 was used to produce the ink composition.

COMPARATIVE EXAMPLE 2

The same method was used as in Example 11, except, instead of using the antibacterial colorant of Chemical Formula 12, C.I. Pigment Red 177 was used to produce the ink composition. Additionally, 3.0 g of TEGO dispers 750W was added as the dispersing agent, and thus, the amount of water was reduced to 74.0 g, and a 0.8 μm filter was used.

COMPARATIVE EXAMPLE 3

The same method was used as in Example 11, except, instead of using the antibacterial colorant of Chemical Formula 12, C.I. Direct Black 51 was used to produce the ink composition.

COMPARATIVE EXAMPLE 4

The same method was used as in Example 11, except, instead of using the antibacterial colorant of Chemical Formula 12, C.I. Acid Black 191 was used to produce the ink composition.

COMPARATIVE EXAMPLE 5

The same method was used as in Example 11, except, instead of using the antibacterial colorant of Chemical Formula 12, C.I. Acid Yellow 23 was used to produce the ink composition.

COMPARATIVE EXAMPLE 6

The same method was used as in Example 11, except, instead of using the antibacterial colorant of Chemical Formula 12, C.I. Pigment Red 57 was used to produce the ink composition. Additionally, 3.0 g of TEGO dispers 750W was added as the dispersing agent, and thus, the amount of water was reduced to 74.0 g, and a 0.8 µm filter was used.

COMPARATIVE EXAMPLE 7

The same method was used as in Example 11, except, instead of using the antibacterial colorant of Chemical Formula 12, C.I. Pigment Black 7 was used to produce the ink composition. Additionally, 3.0 g of TEGO dispers 750W was added as the dispersing agent, and thus, the amount of water was reduced to 74.0 g, and a 0.8 µm filter was used.

COMPARATIVE EXAMPLE 8

A composition was prepared in the same manner as in Comparative Example 1, except for adding 0.1 g of BIT as an antibacterial agent. In this case, the amount of water was reduced to 73.9 g.

COMPARATIVE EXAMPLE 9

A composition was prepared in the same manner as in Comparative Example 2, except for adding 0.1 g of BIT as an antibacterial agent. In this case, the amount of water was reduced to 73.9 g.

COMPARATIVE EXAMPLE 10

A composition was prepared in the same manner as in Comparative Example 3, except for adding 0.1 g of BIT as an antibacterial agent. In this case, the amount of water was reduced to 73.9 g.

COMPARATIVE EXAMPLE 11

A composition was prepared in the same manner as in Comparative Example 4, except for adding 0.1 g of BIT as an antibacterial agent. In this case, the amount of water was reduced to 73.9 g.

COMPARATIVE EXAMPLE 12

A composition was prepared in the same manner as in Comparative Example 5, except for adding 0.1 g of BIT as an antibacterial agent. In this case, the amount of water was reduced to 73.9 g.

COMPARATIVE EXAMPLE 13

A composition was prepared in the same manner as in Comparative Example 6, except for adding 0.1 g of BIT as an antibacterial agent. In this case, the amount of water was reduced to 73.9 g.

COMPARATIVE EXAMPLE 14

A composition was prepared in the same manner as in Comparative Example 7, except for adding 0.1 g of BIT as an antibacterial agent. In this case, the amount of water was reduced to 73.9 g.

EXPERIMENTAL EXAMPLE 1

Storage Stability

The ink compositions produced by Examples 11 to 20 and Comparative Examples 1 to 14 were each placed in heat resistant glass bottles. The bottles were sealed and stored at 60° C. for 2 months. After 2 months, the presence of precipitation at the bottom of the bottles were inspected and recorded in Table 1.

TABLE 1

| | Experimental Example 2: Ames Test | | | | | | | | | | | | | | | | | | | | | | | |
|---|---|---|---|---|---|---|---|---|---|---|---|---|---|---|---|---|---|---|---|---|---|---|---|---|
| | Example | | | | | | | | | | Comparative Example | | | | | | | | | | | | | |
| Class | 11 | 12 | 13 | 14 | 15 | 16 | 17 | 18 | 19 | 20 | 1 | 2 | 3 | 4 | 5 | 6 | 7 | 8 | 9 | 10 | 11 | 12 | 13 | 14 |
| Storage Stability | o | o | o | o | o | o | o | o | o | o | x | x | x | x | x | x | x | x | x | x | x | x | x | x | o: No Presence of Precipitation
x: Presence of Precipitation

TA 98, a salmonella typhimurium tester strain, was added to each of the ink compositions produced by Examples 11 to 20 and Comparative Examples 1 to 14 and cultured in a darkroom at 37° C. for 48 hours. The number of colonies was then counted and recorded in Table 2.

TABLE 2

| | Example | | | | | | | | | |
|---|---|---|---|---|---|---|---|---|---|---|
| Class | 11 | 12 | 13 | 14 | 15 | 16 | 17 | 18 | 19 | 20 |
| Number of Colonies | 73 | 98 | 88 | 92 | 89 | 76 | 97 | 87 | 80 | 95 |

| | Comparative Example | | | | | | | | | | | | | |
|---|---|---|---|---|---|---|---|---|---|---|---|---|---|---|
| Class | 1 | 2 | 3 | 4 | 5 | 6 | 7 | 8 | 9 | 10 | 11 | 12 | 13 | 14 |
| Number of Colonies | 478 | 369 | 410 | 453 | 408 | 429 | 395 | 124 | 102 | 115 | 112 | 109 | 97 | 112 |

As Table 1 and Table 2 indicate, when antibacterial colorants according to the invention as produced in Examples 11 to 20 were used, the storage stability was improved and the numbers of colonies were significantly reduced compared to the Comparative Examples 1 to 7, which employed commonly used colorants and Comparative Examples 8 to 14, which employed commonly used colorants and an antibacterial agent. Accordingly, the antibacterial qualities were improved in the ink compositions of the present invention.

The antibacterial colorant of the present invention combines an antibacterial agent with a commonly used colorant so that the side effects caused by adding a separate antibacterial ingredient to the ink composition are minimized. Further, because the antibacterial quality in the ink is improved, the storage stability is also improved, making the antibacterial colorant valuable in producing ink compositions.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An antibacterial colorant, comprising a colorant molecule having at least one functional group and at least one antibacterial moiety bound thereto by one of: an ester bond and an amide bond,
    wherein the antibacterial agent is one of:
        a carbendazim derivative represented by the following Chemical Formula 1:

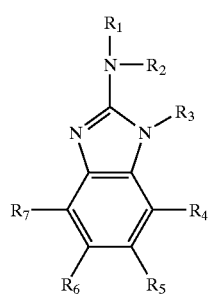

Chemical Formula 1 wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms;

a silane derivative represented by the following Chemical Formula 2:

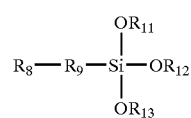

Chemical Formula 2 wherein $R_8$ is selected from the group consisting of a hydrogen atom, a hydroxy group, an amino group, a carboxyl group or salts thereof, and a sulfonic acid group or salts thereof, $R_9$ is selected from the group consisting of a heteroatom of —O—, —N—, —S—, or —P—, a substituted or an unsubstituted alkylene group with 1 to 30 carbon atoms, a substituted or an unsubstituted alkenylene or substituted or unsubstituted alkynylene groups with 2 to 30 carbon atoms, a substituted or an unsubstituted heteroalkylene group with 1 to 30 carbon atoms, a substituted or an unsubstituted arylene group with 6 to 30 carbon atoms, a substituted or an unsubstituted arylalkylene group with 6 to 30 carbon atoms, a substituted or an unsubstituted heteroarylene group with 6 to 30 carbon atoms, a substituted or an unsubstituted heteroarylalkylene group with 6 to 30 carbon atoms, and $R_{11}$, $R_{12}$, and $R_{13}$ each independently is selected from the group consisting of a hydrogen atom, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms; and a combination thereof.

2. The antibacterial colorant of claim 1, wherein the antibacterial agent is a carbendazim derivative of Chemical Formula 1 represented by the following Chemical Formula 3:

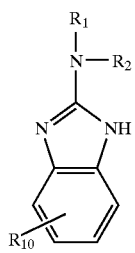

Chemical Formula 3 wherein $R_1$ is selected from the group consisting of a hydrogen atom, a hydroxy group and a carboxyl group, and $R_2$ and $R_{10}$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a sulfonic acid group or salts thereof, a phosphoric acid group or salts thereof, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms.

3. The antibacterial colorant of claim 1, wherein the colorant molecule is one of: a dye and a pigment.

4. An ink composition comprising:
   a carrier medium; and
   an antibacterial colorant, comprising a colorant molecule having at least one functional group and at least one antibacterial moiety bound thereto by one of: an ester bond and an amide bond, wherein the antibacterial agent is one of:
   a carbendazim derivative represented by the following Chemical Formula 1:

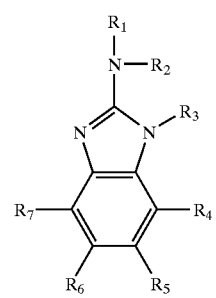

Chemical Formula 1 wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms;

a silane derivative represented by the following Chemical Formula 2:

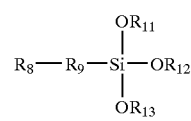

Chemical Formula 2 wherein $R_8$ is selected from the group consisting of a hydrogen atom, a hydroxy group, an amino group, a carboxyl group or salts thereof, and a sulfonic acid group or salts thereof, $R_9$ is selected from the group consisting of a heteroatom of —O—, —N—, —S—, or —P—, a substituted or an unsubstituted alkylene group with 1 to 30 carbon atoms, a substituted or an unsubstituted alkenylene or substituted or unsubstituted alkynylene groups with 2 to 30 carbon atoms, a substituted or an unsubstituted heteroalkylene group with 1 to 30 carbon atoms, a substituted or an unsubstituted arylene group with 6 to 30 carbon atoms, a substituted or an unsubstituted arylalkylene group with 6 to 30 carbon atoms, a substituted or an unsubstituted heteroarylene group with 6 to 30 carbon atoms, a substituted or an unsubstituted heteroarylalkylene group with 6 to 30 carbon atoms, and $R_{11}$, $R_{12}$, and $R_{13}$ each independently is selected from the group consisting of a hydrogen atom, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms; and a combination thereof.

5. The ink composition of claim 4, wherein the amount of the antibacterial colorant is 1 to 20 parts by weight per 100 parts by weight of the composition.

6. The ink composition of claim 4, wherein the carrier medium is one of: water, at least one organic solvent, and a mixture thereof.

7. The composition according to claim 4, wherein when the carrier medium is a mixture of water with at least one organic solvent, the organic solvent is added to the composition in an amount of 5 to 50 parts by weight based on 100 parts by weight of the composition.

8. The ink composition of claim 6, wherein the at least one organic solvent is selected from the group consisting of: alcohols, ketones, esters, polyhydric alcohols, lower alkylethers, nitrogenous chemical compounds, and sulfurous chemical compounds.

9. The composition according to claim 4, further comprising at least one selected from the group consisting of a dispersing agent, a viscosity control agent, a surfactant, a storage stabilizer, a humectant, and a metallic oxide.

10. An ink composition comprising:
a carrier medium; and
an antibacterial colorant, comprising a colorant molecule having at least one functional group and at least one antibacterial moiety bound thereto by one of: an ester bond and an amide bond, wherein the antibacterial agent is a carbendazim derivative represented by the following Chemical Formula 1:

Chemical Formula 1

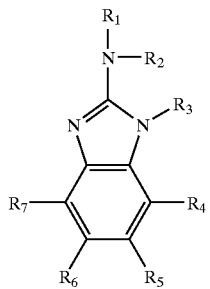

wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms.

11. An ink composition comprising:
a carrier medium; and
an antibacterial colorant, comprising a colorant molecule having at least one functional group and at least one antibacterial moiety bound thereto by one of: an ester bond and an amide bond, wherein the antibacterial agent is a carbendazim derivative of Chemical Formula 1 represented by the following Chemical Formula 3:

Chemical Formula 3

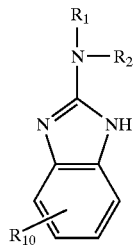

wherein $R_1$ is selected from the group consisting of a hydrogen atom, a hydroxy group and a carboxyl group, and $R_2$ and $R_{10}$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a sulfonic acid group or salts thereof, a phosphoric acid group or salts thereof, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms.

12. An ink composition comprising:
a carrier medium; and
an antibacterial colorant, comprising a colorant molecule having at least one functional group and at least one antibacterial moiety bound thereto by one of: an ester bond and an amide bond, wherein the antibacterial agent is a silane derivative represented by the following Chemical Formula 2:

Chemical Formula 2

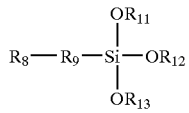

wherein $R_8$ is selected from the group consisting of a hydrogen atom, a hydroxy group, an amino group, a carboxyl group or salts thereof, and a sulfonic acid group or salts thereof, $R_9$ is selected from the group consisting of a heteroatom of —O—, —N—, —S—, or —P—, a substituted or an unsubstituted alkylene group with 1 to 30 carbon atoms, a substituted or an unsubstituted alkenylene or substituted or unsubstituted alkynylene groups with 2 to 30 carbon atoms, a substituted or an unsubstituted heteroalkylene group with 1 to 30 carbon atoms, a substituted or an unsubstituted arylene group with 6 to 30 carbon atoms, a substituted or an unsubstituted arylalkylene group with 6 to 30 carbon atoms, a substituted or an unsubstituted heteroarylene group with 6 to 30 carbon atoms, a substituted or an unsubstituted heteroarylalkylene group with 6 to 30 carbon atoms, and $R_{11}$, $R_{12}$, and $R_{13}$ each independently is selected from the group consisting of a hydrogen atom, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms.

13. An ink composition comprising:
a carrier medium; and
an antibacterial colorant, comprising a colorant molecule having at least one functional group and at least one antibacterial moiety bound thereto by one of: an ester bond and an amide bond, wherein the colorant molecule is one of: a dye and a pigment,
wherein the antibacterial agent is:
a carbendazim derivative represented by the following Chemical Formula 1:

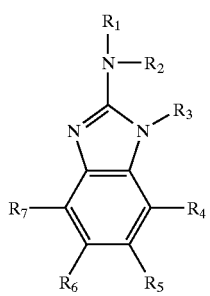

Chemical Formula 1 wherein $R_1$ is selected from the group consisting of a hydrogen atom, a hydroxy group, an amino group, a carboxyl group or salts thereof, a sulfonic acid group or salts thereof or a phosphoric acid group or salts thereof, and $R_2$, $R_3$, $R_4$, $R_5$, $R_6$ and $R_7$ each independently is selected from the group consisting of a hydrogen atom, a halogen atom, a hydroxy group, a nitro group, a cyano group, an amino group, an amidino group, a hydrazine group, a hydrazone group, a carboxyl group or salts thereof, a phosphoric acid group or salts thereof, a substituted or an unsubstituted alkyl group with 1 to 30 carbon atoms, a substituted or an unsubstituted alkylthio group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroalkyl group with 1 to 30 carbon atoms, a substituted or an unsubstituted heteroaryl group with 6 to 30 carbon atoms, and a substituted or an unsubstituted heteroarylalkyl group with 6 to 30 carbon atoms;
a silane derivative represented by the following Chemical Formula 2:

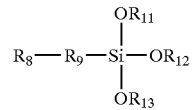

Chemical Formula 2 wherein $R_8$ is selected from the group consisting of a hydrogen atom, a hydroxy group, an amino group, a carboxyl group or salts thereof, and a sulfonic acid group or salts thereof, $R_9$ is selected from the group consisting of a heteroatom of —O—, —N—, —S—, or —P—, a substituted or an unsubstituted alkylene group with 1 to 30 carbon atoms, a substituted or an unsubstituted alkenylene or substituted or unsubstituted alkynylene groups with 2 to 30 carbon atoms, a substituted or an unsubstituted heteroalkylene group with 1 to 30 carbon atoms, a substituted or an unsubstituted arylene group with 6 to 30 carbon atoms, a substituted or an unsubstituted arylalkylene group with 6 to 30 carbon atoms, a substituted or an unsubstituted heteroarylene group with 6 to 30 carbon atoms, a substituted or an unsubstituted heteroarylalkylene group with 6 to 30 carbon atoms, and $R_{11}$, $R_{12}$, and $R_{13}$ each independently is selected from the group consisting of a hydrogen atom, a substituted or an unsubstituted alkyl group with 1 to 30 carbon atoms, a substituted or an unsubstituted alkenyl or a substituted or an unsubstituted alkynyl group with 2 to 30 carbon atoms, a substituted or an unsubstituted heteroalkyl group with 1 to 30 carbon atoms, a substituted or an unsubstituted aryl group with 6 to 30 carbon atoms, a substituted or an unsubstituted arylalkyl group with 6 to 30 carbon atoms, a substituted or an unsubstituted heteroaryl group with 6 to 30 carbon atoms, and a substituted or an unsubstituted heteroarylalkyl group with 6 to 30 carbon atoms; and
a combination thereof.

14. The ink composition of claim 8, wherein the alcohol/alcohols is/are selected from the group consisting of: methylalcohol, ethylalcohol, n-propylalcohol, isopropylalcohol, n-butylalcohol, sec-butylalcohol, and t-butylalcohol, and isobutylalcohol.

15. The ink composition of claim 8, wherein the ketone/ketones is/are selected from the group consisting of: acetone, methylethylketone and diacetonealcohol.

16. The ink composition of claim 8, wherein the ester/esters is/are selected from the group consisting of: ethyl acetate and ethyl lactate.

17. The ink composition of claim 8, wherein the polyhydric alcohol/polyhydric alcohols is/are selected from the group consisting of: ethyleneglycol, diethyleneglycol, triethyleneglycol, propyleneglycol, butyleneglycol, 1,4-butandiol, 1,2,4-butantriol, 1,5-pentandiol, 1,2,6-hexanetriol, hexyleneglycol, glycerol, glycerol ethoxylate, and trimethylolpropane ethoxylate.

18. The ink composition of claim 8, wherein the lower alkylether/alkylethers is/are selected from the group consisting of: ethyleneglycol monomethylether, ethyleneglycol monoethylether, diethyleneglycol methylether, diethyleneglycol ethylether, triethyleneglycol monomethylether, and triethyleneglycol monoethyl ether.

19. The ink composition of claim 8, wherein the nitrogenous chemical compound/compounds is/are selected from the group consisting of: 2-pyrrolidone and N-methyl-2-pyrrolidone.

20. The ink composition of claim 8, wherein the sulfurous chemical compound/compounds is/are selected from the group consisting of: dimethyl sulfoxide, tetramethylene sulfone and thioglycol.

21. The ink composition of claim 7, wherein the at least one organic solvent is selected from the group consisting of: alcohols, ketones, esters, polyhydric alcohols, lower alkylethers, nitrogenous chemical compounds, and sulfurous chemical compounds.

22. The ink composition of claim 21, wherein the alcohol/alcohols is/are selected from the group consisting of: methylalcohol, ethylalcohol, n-propylalcohol, isopropylalcohol, n-butylalcohol, sec-butylalcohol, and t-butylalcohol, and isobutylalcohol.

23. The ink composition of claim 21, wherein the ketone/ketones is/are selected from the group consisting of: acetone, methylethylketone and diacetonealcohol.

24. The ink composition of claim 21, wherein the ester/esters is/are selected from the group consisting of: ethyl acetate and ethyl lactate.

25. The ink composition of claim 21, wherein the polyhydric alcohol/polyhydric alcohols is/are selected from the group consisting of: ethyleneglycol, diethyleneglycol, triethyleneglycol, propyleneglycol, butyleneglycol, 1,4-butandiol, 1,2,4-butantriol, 1,5-pentandiol, 1,2,6-hexanetriol, hexyleneglycol, glycerol, glycerol ethoxylate, and trimethylolpropane ethoxylate.

26. The ink composition of claim 21, wherein the lower alkylether/alkylethers is/are selected from the group consisting of: ethyleneglycol monomethylether, ethyleneglycol monoethylether, diethyleneglycol methylether, diethyleneglycol ethylether, triethyleneglycol monomethylether, and triethyleneglycol monoethyl ether.

27. The ink composition of claim 21, wherein the nitrogenous chemical compound/compounds is/are selected from the group consisting of: 2-pyrrolidone and N-methyl-2-pyrrolidone.

28. The ink composition of claim 21, wherein the sulfurous chemical compound/compounds is/are selected from the group consisting of: dimethyl sulfoxide, tetramethylene sulfone and thioglycol.

* * * * *